United States Patent [19]

Dunham

[11] Patent Number: 5,783,227
[45] Date of Patent: Jul. 21, 1998

[54] CATHETER BALLOON FOLDING DEVICE

[75] Inventor: Susan L. Dunham, Pembroke Pines, Fla.

[73] Assignee: Cordis Corporation, Miami Lakes, Fla.

[21] Appl. No.: 589,766

[22] Filed: Jan. 22, 1996

[51] Int. Cl.$^6$ .................................................. B29C 53/08
[52] U.S. Cl. ............................ 425/318; 425/391; 425/392; 425/395
[58] Field of Search ............................ 264/523, 535, 264/573, 295; 425/393, 392, 395, 318, 391

[56] References Cited

U.S. PATENT DOCUMENTS

| | | | |
|---|---|---|---|
| 3,012,274 | 12/1961 | Levy | 425/392 |
| 5,015,231 | 5/1991 | Keith et al. | 604/96 |
| 5,037,392 | 8/1991 | Hillstead | 604/96 |
| 5,087,246 | 2/1992 | Smith | 604/96 |
| 5,147,302 | 9/1992 | Euteneuer et al. | 604/103 |
| 5,209,799 | 5/1993 | Vigil | 156/156 |
| 5,226,887 | 7/1993 | Farr et al. | 604/96 |
| 5,342,307 | 8/1994 | Euteneuer et al. | 604/103 |
| 5,350,361 | 9/1994 | Tsukashima et al. | 264/573 |
| 5,456,666 | 10/1995 | Campbell et al. | 604/96 |

FOREIGN PATENT DOCUMENTS

| | | | |
|---|---|---|---|
| 418611 | 9/1925 | Germany | 425/395 |
| 56-156904 | 12/1981 | Japan | 425/392 |
| 59-38047 | 3/1984 | Japan | 425/392 |

*Primary Examiner*—Robert Davis
*Attorney, Agent, or Firm*—Lockwood, Alex, Fitzgibbon & Cummings

[57] ABSTRACT

A device for making folds in an angioplasty balloon while attached to the distal and portion of an angioplasty catheter has a plurality of press members. Each press member has a substantially planar balloon-contacting surface and the press members are interconnected so that the balloon contacting surfaces of opposing press members confront each other. One or more of the press members includes a longitudinal passage formed in an associated balloon contacting surface which receives the catheter shaft so that the balloon may be folded between the surfaces flanking the passage.

18 Claims, 2 Drawing Sheets

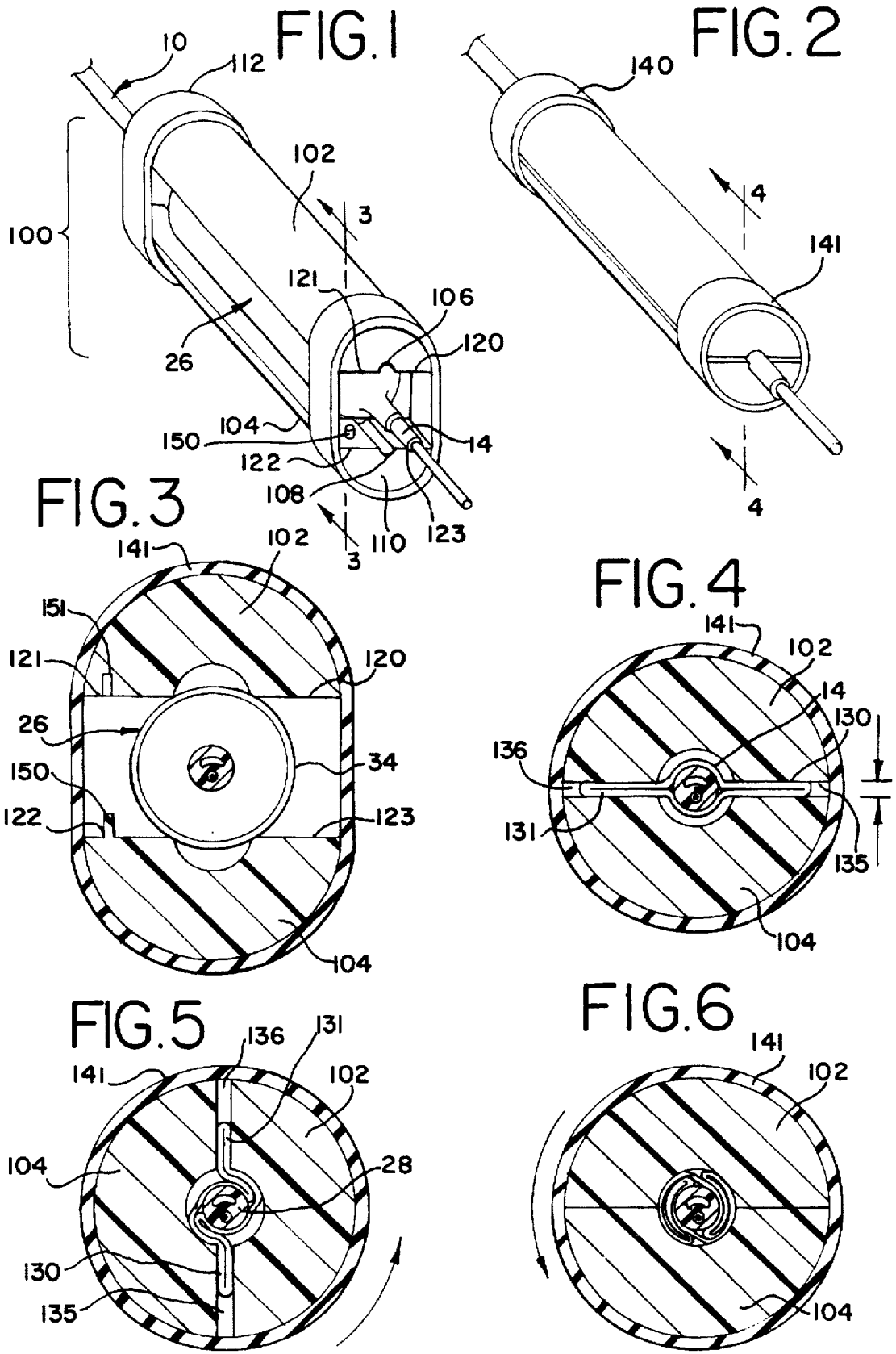

CATHETER BALLOON FOLDING DEVICE

BACKGROUND AND SUMMARY OF THE INVENTION

The present invention relates generally to the use and preparation of balloon catheters for angioplasty and other surgical procedures and more specifically, to a device for folding such balloons upon themselves and around a catheter shaft.

The use of angioplasty to relieve blockages, or occlusions, of blood vessels has increased significantly in recent years. Angioplasty typically involves the insertion of an inflatable balloon into an occluded blood vessel and positioning the balloon at the occlusion. The balloon is then rapidly inflated and deflated in order to expand the occlusion and restore the blood vessel to its original, workable size.

Angioplasty catheters which are used for these procedures typically include a guidewire, a balloon catheter having a guide lumen which receives the guidewire, an inflation lumen extending to the distal end of the catheter and an inflatable balloon positioned at the distal end of a catheter over an opening of the inflation lumen. The balloons used with such catheters typically have an inflatable body portion disposed between two leg portions. The leg portions have a diameter which is slightly less than the diameter of the catheter at its distal end in order to provide a tight seal which permits inflation and deflation of the balloon. The body portion has a diameter greater than that of the leg portions and the catheter shaft. Typically this diameter corresponds to the actual diameter of the balloon when inflated, particularly when a non-expandable material is used for construction of the balloon. The inflated diameter of angioplasty balloons may range anywhere from between 1.5 to 4.0 mm, while the diameter of the catheter at its distal end is in the order of 1mm. The excess balloon material, when deflated, must be folded, or rolled, upon the catheter distal end portion to facilitate insertion of the balloon into the blood vessel. When so folded, the balloon will not impinge upon the walls of the blood vessel as it is being positioned within the blood vessel at the site of the occlusion. This folding is typically accomplished by manually rolling the balloon onto the shaft. Because of the very small dimensions of these balloons, it is difficult and time consuming to ensure that the balloon is accurately folded upon itself.

The present invention therefore is directed to a device for forming radial folds, or pleats, in angioplasty balloons while they are attached to the catheter shaft and which simplifies folding of the balloon onto the catheter shaft. The present invention therefore ensures that the proper folded configuration of the balloon on the catheter distal end portion is achieved prior to insertion of the balloon catheter into the blood vessel.

In one principal aspect, the present invention includes a balloon press having two balloon contacting members with a central channel extending along at least one of the balloon contacting members. This channel is aligned with the catheter shaft and encloses it so that confronting surfaces of the balloon contacting members may then be brought into contact with the balloon to define a desired number of folds in the balloon. This contact is achieved by pressing the contacting members toward each other until they contact the balloon and press portions of the balloon to form one or more folds which extend radially outwardly from the catheter shaft.

In another aspect, the present invention includes one or more means to impart a folding pressure to the balloon contacting members. In a preferred embodiment, these pressure imparting means includes a pair of elastic bands which surround the balloon-contacting members and apply a force thereto to draw the balloon-contacting members together in a manner that the opposing planar surfaces thereof are aligned with each other to substantially confront each other. The balloon is compressed, or flattened, between these surfaces and deflated during the forming of these folds.

In yet another aspect of the present invention, the balloon-contacting members are preferably formed from a lubricous, or non-sticking material which will not engage the balloon in a manner which causes the balloon to stick the confronting surfaces of the balloon-contacting members and bind during rotation of either the folding device or catheter assembly. A space having a thickness approximately equal to the thickness of the balloon fold may be defined between these confronting surfaces, and the balloon folds may be easily withdrawn from this space in during such rotation in order to facilitate wrapping of the balloon folds upon the catheter shaft.

In still yet another aspect of the present invention, a balloon press has a central cavity extending along at least a portion of its length which receives a catheter balloon therein. The press also has one or more means by which pressure may be applied to the press in order to bring the balloon contacting surface or surfaces thereof into contact with the catheter balloon in the central cavity to define a desired number of folds in the balloon.

Accordingly, it is an object of the present invention to provide a folding device for forming folds in angioplasty balloons which is compact and which reliably forms one or more folds in an angioplasty balloon and holds the folds in place during the wrapping.

Another object of the present invention is to provide a balloon for a catheter balloon folding device suitable for use with percutaneous transluminal coronary angioplasty (PTCA) and other catheters, the device comprising a balloon press with multiple confronting balloon-contacting surfaces disposed thereon, the press further having a centrally disposed channel therein which receives and encloses the shaft of a balloon catheter assembly, the confronting balloon-contacting surfaces lying adjacent the channel to thereby define at least one balloon contacting region which contacts and compresses the balloon outside of the catheter shaft and creates a radial fold in the balloon.

Still another object of the present invention is to provide a method for wrapping an angioplasty balloon around the distal end portion of an angioplasty catheter, wherein the method comprises the steps of inflating the balloon to a distended state, providing a balloon press, placing the inflated balloon between at least two confronting balloon-engagement surfaces of the balloon press, drawing the confronting balloon-engagement surfaces together until they contact portions of the balloon, deflating the balloon during such contact to thereby form at least one fold in the balloon body portion which extends radially outwardly from the catheter shaft and rotating one of the balloon press and catheter to circumferentially wrap the balloon fold upon the catheter shaft.

These and other objects, features and advantages of the present invention will be clearly understood through a consideration of the following detailed description.

BRIEF DESCRIPTION OF THE DRAWINGS

In the course of the following detailed description, reference will be frequently made to the accompanying drawings in which:

3

Figure 7:
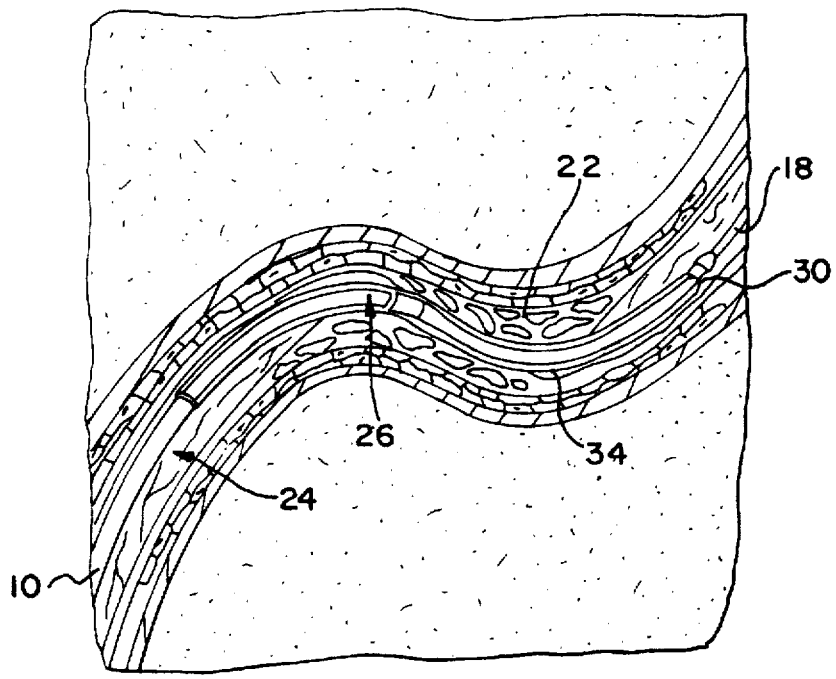
Figure 8:
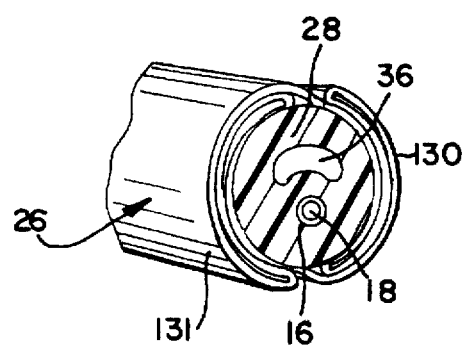
Figure 9:
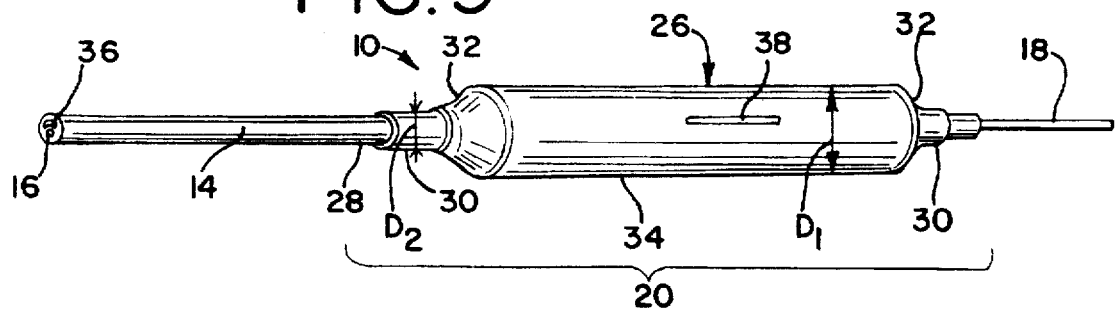

FIG. 1 is a perspective view of a balloon folding device constructed in accordance with the principles of the present invention, illustrating a balloon catheter assembly in place in a ready position within the device;

FIG. 2 is a perspective view of the balloon folding device of FIG. 1 illustrating the two opposing press members of the balloon folding device in an operational position where the press members have been drawn toward each other to effect at least one radial fold in the balloon;

FIG. 3 is a cross-sectional view taken through the folding device of FIG. 1 along line 3—3 thereof;

FIG. 4 is a cross-sectional view taken through the folding device of FIG. 2 along line 4—4 thereof;

FIG. 5 is a cross-sectional view through the balloon folding device of FIG. 2 illustrating how the balloon folds are wrapped around the catheter shaft by rotating either the balloon folding device or the catheter shaft approximately one-quarter turn;

FIG. 6 is the same view as FIG. 5 but illustrating rotation of the balloon folding device a predesired number of turns to wrap the balloon folds completely around the catheter shaft;

FIG. 7 is a cross-sectional view of a blood vessel with a balloon catheter inserted therein near the site of an occlusion;

FIG. 8 is an enlarged sectional view of a balloon wrapped around its catheter shaft; and, FIG. 9 is an elevational view of the distal end of a balloon catheter assembly illustrating the balloon inflated into a distended position.

DETAILED DESCRIPTION OF THE PREFERRED EMBODIMENTS

A PCTA balloon catheter assembly is illustrated generally at 10 in FIG. 9. Such balloon catheter assemblies 10 are commonly used in angioplasty procedures for clearing partially or substantially blocked blood vessels. The catheter assembly 10 is typically inserted into a blood vessel and moved through the vessel to the site of the blockage where it is inflated and deflated to compress and reduce the blockage.

The catheter assembly 10 is conventional in construction and is seen to include an elongated catheter 14 with a guidewire lumen 16 extending longitudinally therethrough. A guidewire 18, which is received within the lumen 16, permits positioning of the distal end 20 of the catheter assembly 10 within an occlusion 22 of the blood vessel 24 as illustrated in FIG. 7.

An inflatable angioplasty balloon 26 is positioned on the catheter assembly 10 along the shaft portion 28 thereof. The balloon 26 includes two opposing leg portions 30 illustrated in FIG. 9 as having a diameter slightly less than the overall diameter of the catheter shaft portion 28 so that the leg portions 30 firmly engage the catheter shaft portion 28 to provide a seal thereagainst during inflation and deflation of the balloon 26. Annular transition portions 32 are provided adjacent the balloon leg portions 30 and ramp up to a body portion 34 of the balloon 26 which has a working length which extends between the transition portions 32. The body portion 34 of the balloon 26 has an overall working diameter $D_1$ when inflated, which is greater than the diameter $D_2$ of the balloon leg portions 30.

As is known in the art, the body portion 34 is inflated under pressure of a fluid, typically a saline or radiopaque solution, injected through an inflation lumen 36 of the catheter 14. This lumen 36 extends approximately the full length of the catheter 14 and terminates in an opening 38 on the distal end 20 of the catheter assembly 10 which is located adjacent the balloon body portion 34 between the two leg portions 30 thereof.

It will be understood that the catheter assembly 10 depicted in the Figures is for purposes of example and not limitation. Although the catheter assembly 10 illustrated depicts the inflation lumen 36 and guidewire lumen 16 as formed within the catheter shaft portion 28 at the distal end of the catheter assembly 10, it is contemplated that the invention may be used with other catheter constructions such as a catheter distal end wherein the inflation and guidewire lumens are coaxially arranged.

When inflated, the balloon expands under fluid pressure to its working diameter $D_1$ within the body vessel 24 against the occlusion 22 to compress the occlusion and thereby open the blood vessel 24. As is known in the art, these balloons or such balloon may be formed from a variety of materials, such as PET (polyethylene terephthalate) which has relatively no expansion characteristics to nylon, which has highly controlled expansion characteristics. No matter what type of material is used for the balloon 26, the body portion 34 of the balloon 26 extends outwardly from the catheter shaft portion 28 of the catheter assembly 10 when the balloon 26 is in either an inflated or uninflated state. This extension of the balloon 26 is large compared to the diameter of the catheter shaft portion 28. The diameters $D_1$ of the balloon body portions 34 may vary from 1.5 to 3.5 mm while that of the catheter is in the order of about 1 mm. Thus, the balloon body portion 34, inasmuch as it extends from the catheter shaft portion 28, may prove to be a temporary impediment to the insertion of the balloon catheter into a blood vessel 24 because it may flap around and catch on portions, or walls, of the blood vessel 24. In order to prevent this problem, the body portion 34 of the balloon 26 is typically wrapped around the catheter shaft portion 28 prior to insertion of the catheter assembly 10 into the blood vessel 24.

Turning now to FIG. 1, a balloon folding device 100 constructed in accordance with the principles of the present invention is illustrated. The balloon folding device preferably includes two elongated press members 102, 104, each press member being illustrated as a separate member which cooperate together to define a central passage 106, preferably in the form of a semi-circular channel 108. This passage 106 is adapted to receive the distal end 20 of the catheter assembly 10 therein and preferably substantially encloses the catheter shaft portion 28. The passage 106 permits the user to properly position the catheter assembly 10 and the balloon 26 within the device 100.

When properly positioned, the working length of the body portion 34 of the balloon 26 lies between the ends 110, 112 of the device 100. In this regard, it may be desirable to choose a length of the press members 102, 104 which is greater than most working lengths of balloons. The press members 102, 104 are pulled apart so that the catheter distal end 20 may be inserted into the device 100. Once inserted, the balloon 26 is inflated so that it reaches a distended, or expanded, position within the device 100, as shown in cross-section in FIG. 3. The opposing press members 102, 104, of the device 100 are then brought together, as illustrated in FIG. 4, so that the balloon is compressed therebetween. The balloon 26 is typically deflated as the press members 102, 104 are drawn together, with the inflation medium exiting from the balloon 26 by way of the catheter inflation opening 38, or a vacuum may be applied to the catheter inflation lumen 36 to deflate the balloon 26 while it is being pressed, the pressing action being applied to the balloon 26 by the resilient members 140, 141.

In order to provide effective folding of the balloon body portion 34, the press members 102, 104 preferably each include at least one planar surface which is brought into contact with the balloon 26 during pressing. Two such planar surfaces 120, 121 and 122, 123 are shown on each press member 102, 104 in the Figures. These balloon press surfaces confront each other and serve as a means to press portions of the balloon together between them, as illustrated in FIG. 4, and thereby define one or more folds 130, 131 in the balloon 26. These folds may be aptly characterized as "radial" folds because they extend radially outwardly from the catheter shaft portion 28.

The central passage 106 of the folding device 100 encloses the catheter shaft 14 during such pressing and prevents the planar balloon-contacting surfaces 120-123 from contacting the shaft and pinching the balloon against the catheter shaft portion 28. When pressed together, two slight spaces 135, 136 are defined between the confronting surfaces 120-123 of the press members 102, 104. The thickness of these spaces may be generally equal to the thickness of the balloon fold, or twice the thickness of the balloon. These spaces result from the thickness of the balloon material. However, the spaces may also be independently formed in the folding device such as machining the contacting surfaces 120-123 of the press members 102, 104.

In an important aspect of the present invention, the device 100 may be further used, after pressing, to fold the balloon radial folds 130, 131 around the catheter shaft 14 for insertion of the catheter assembly 10 into a patient's blood vessel. In this regard, the balloon press sections 102, 104 are preferably formed from a inherently lubricous material, such as PTFE or the like, so that the confronting balloon contacting surfaces 120-123 do not engage the balloon radial folds 130, 131 in such a manner which would prevent their withdrawal from the press spaces 135, 136 formed between the balloon press sections 102, 104. Thus, when the balloon has been folded and the press sections 102, 104 are brought into alignment and engagement with each other, the user may turn either the device or the catheter shaft 14. This turning, or twisting, movement will cause the folds 130, 131 to wind upon the catheter shaft 14 in the direction of turning as shown in FIGS. 5 and 6.

In FIG. 5, the folding device 100 has been turned approximately one-quarter turn while the catheter assembly 10 has been held steady. This turning has resulted in the two balloon folds 130, 131 illustrated wrapping themselves upon the catheter shaft portion 28. This wrapping is partially defined in FIG. 5 and fully defined in FIG. 6, where the folding device 100 has been completely rotated so that the balloon folds 130, 131 are completely wrapped around the catheter shaft portion 28. (FIG. 7).

Alternate embodiments of the folding device may include more than two press members. These multiple press members would include more than the four confronting surfaces shown in FIGS. 1-6. In such embodiments, the press member may be aligned by a suitable means such as the registration posts 150 formed on one press member and corresponding openings 151 formed in another, opposing press member.

Still other embodiments of the folding device may include press members which are interconnected together.

The present invention further includes a means for urging the press sections 102, 104 toward each other which, as illustrated in FIGS. 1-6, include a pair of resilient members 140, 141 which substantially surround the press sections 102, 104 as illustrated near the ends 110, 112 thereof. These resilient members may take the form of elastic bands or other suitable members. The resilient members need not be positioned directly at the ends of the folding device, but may be disposed at other locations and the members may include one, elongated hollow sleeve member.

While the preferred embodiment of the invention have been shown and described, it will be understood by those skilled in the art the changes or modifications may be made thereto without departing from the true spirit and scope of the invention.

I claim:

1. A device for configuring an inflatable balloon of a balloon catheter assembly to a distal end portion of the catheter by forming folds in the balloon in a manner such that said fold formed in said balloon may be wound around said catheter, wherein the balloon includes a foldable body portion having a preselected working length, the balloon body portion enclosing a portion of the catheter distal end portion and having a diameter greater than a diameter of said catheter distal end portion, the device comprising: a press body having at least two balloon-contacting planar surfaces disposed thereon, the balloon-contacting surfaces of said press body being disposed in a generally confronting relationship with each other; a longitudinal passage disposed in said press body, the passage being further disposed adjacent at least one of said balloon-contacting surfaces, said passage substantially enclosing said distal end portion of said balloon catheter assembly therein when said distal end portion is placed into said device such that portions of said balloon, when inflated, extend away from said distal end portion and contact at least one of said balloon-contacting surfaces of said press body; and, means for urging said balloon-contacting surfaces together when they are substantially aligned together in face-to-face contact and pressing a portion of said balloon into a space between said balloon-contacting surfaces to form a fold in said balloon.

2. The balloon configuring device as defined in claim 1, wherein said urging means includes at least one elastic element substantially surrounding said press body.

3. The balloon configuring device as defined in claim 1, wherein said balloon press body urging means includes two elastic bands encircling said press body proximate to opposing end portions of said device.

4. The balloon configuring device as defined in claim 1, wherein said balloon-contacting surfaces of said press body are formed from a lubricous material.

5. The balloon configuring device as defined in claim 1, wherein said longitudinal passage includes an arcuate channel.

6. The balloon configuring device as defined in claim 1, wherein said confronting balloon-contacting surfaces have a width which is greater than said inflated diameter of said balloon.

7. The balloon configuring device as defined in claim 1, further including means for aligning said press body balloon-contacting surfaces into said confronting relationship.

8. The balloon configuring device as defined in claim 7, wherein said press body alignment means includes registration members corresponding openings formed therein.

9. The ballon configuring device as defined in claim 1, wherein said press body includes at least two balloon press members that are generally semi-circular in cross section.

10. The balloon configuring device as defined in claim 1, wherein said press body includes at least two balloon press members.

11. The balloon configuring device as defined in claim 10, wherein each of said balloon press members includes one of said two balloon-contacting surfaces.

12. A press for forming folds in an angioplasty balloon of an angioplasty catheter assembly wherein the catheter assembly includes an elongated catheter with a distal end portion and an inflatable balloon disposed on said catheter distal end portion, the balloon having two leg portions disposed at opposite ends of said balloon which engage said catheter distal end portion, said balloon further having a foldable, inflatable body portion intermediate of said balloon leg portions, said balloon body portion having a diameter greater than a diameter of said catheter distal end portion, the press comprising, in combination:

at least two elongated press members having a length which exceeds a working length of said balloon so that when said balloon is inserted into said press said balloon body portion lies between opposing ends of said press members, each of said press members including at least one substantially planar balloon-contacting surface, said press member and their associated balloon-contacting surfaces being held together by retaining means which exerts a force upon said press members to draw their balloon-contacting surfaces together, but permitting said press members to be moved apart to define an opening in said press which receives said catheter distal end portion, said press further including an elongated passage extending through said press in at least one of said balloon-contacting surfaces, the passage receiving and substantially enclosing a shaft portion of said catheter distal end portion when inserted into said press opening, said balloon-contacting surfaces lying adjacent to said passage, whereby when said catheter distal end portion is inserted into said press opening and said balloon is inflated and said press members are drawn together by said retaining means, said balloon-contacting surfaces contact an exterior surface of said inflatable balloon and define at least one folded portion in said balloon between said balloon-contacting surfaces when said press members are drawn together, the balloon folded portion extending outwardly from said catheter assembly distal end portion.

13. The angioplasty balloon press as defined in claim 12, wherein said press member retaining means includes at least one elastic band surrounding said press members.

14. The angioplasty balloon press as defined in claim 12, wherein said passage is formed from at least two aligned channels formed in opposing balloon-contacting surfaces.

15. The angioplasty balloon press as defined in claim 12, wherein said press members have a width along their balloon-contacting surfaces which is greater than a width of said inflated balloon.

16. The angioplasty balloon press as defined in claim 12, wherein said press member balloon-contacting surfaces are lubricous.

17. A press for forming folds in an angioplasty balloon of an angioplasty catheter assembly wherein the catheter assembly includes an elongated catheter with a distal end portion and an inflatable balloon disposed on said catheter distal end portion, the balloon having two leg portions disposed at opposite ends of said balloon which engage said catheter distal end portion, said balloon further having an inflatable body portion intermediate of said balloon leg portions, said balloon body portion having a diameter greater than a diameter of said catheter distal end portion, the press comprising, in combination:

at least two elongated press members of a semicircular configuration having a length which exceeds a working length of said balloon so that when said balloon is inserted into said press said balloon body portion lies between opposing ends of said press members, each of said press members including at least one substantially planar balloon-contacting surface, said press member and their associated balloon-contacting surfaces being held together by retaining means which exerts a force upon said press members to draw their balloon-contacting surfaces together, but permitting said press members to be moved apart to define an opening in said press which receives said catheter distal end portion, said press further including an elongated passage extending through said press in at least one of said balloon-contacting surfaces, the passage receiving and substantially enclosing a shaft portion of said catheter distal end portion when inserted into said press opening, said balloon-contacting surfaces lying adjacent to said passage, whereby when said catheter distal end portion is inserted into said press opening and said balloon is inflated and said press members are drawn together by said retaining means, said balloon-contacting surfaces contact an exterior surface of said inflatable balloon and define at least one folded portion in said balloon between said balloon-contacting surfaces when said press members are drawn together, the balloon folded portion extending outwardly from said catheter assembly distal end portion.

18. A device for configuring an inflatable balloon of a balloon catheter assembly to a distal end portion of the catheter by forming folds in the balloon, wherein the balloon includes a body portion having a preselected working length, the balloon body portion enclosing a portion of the catheter distal end portion and having a diameter greater than a diameter of said catheter distal end portion, the device comprising: a press body having at least two balloon-contacting surfaces disposed thereon; a longitudinal passage disposed in said press body adjacent at least one of said balloon-contacting surfaces, said passage substantially enclosing said distal end portion of said balloon catheter assembly therein, whereby when said catheter distal end portion is placed into said device such that portions of said balloon, when inflated, extend away from said distal end portion and contact at least one of said balloon-contacting surfaces of said press body, said device including means for urging said balloon-contacting surfaces together, said urging means including at least one elastic element surrounding said press body.

* * * * *